United States Patent [19]

Zboril

[11] Patent Number: 5,342,499
[45] Date of Patent: Aug. 30, 1994

[54] MONITORING AND CONTROL OF PROCESS STREAMS AT ELEVATED TEMPERATURES

[75] Inventor: Vaclav G. Zboril, Kingston, Canada

[73] Assignee: Du Pont Canada Inc., Mississauga, Canada

[21] Appl. No.: 53,623

[22] Filed: Mar. 25, 1993

Related U.S. Application Data

[62] Division of Ser. No. 829,845, Jan. 31, 1992, Pat. No. 5,213,668.

[30] Foreign Application Priority Data

Feb. 4, 1991 [GB] United Kingdom ................ 9102371

[51] Int. Cl.$^5$ ............................................. G01N 27/26
[52] U.S. Cl. ................................. 204/409; 204/416; 204/433; 204/435
[58] Field of Search ................ 204/416, 433, 435, 409

[56] References Cited

U.S. PATENT DOCUMENTS 3,681,205  8/1972  Ducksbury et al. ................. 204/433
4,242,189 12/1980  Dobson ................................. 204/416

OTHER PUBLICATIONS

J. Electrochem. Soc., vol. 132, No. 8, pp. 1866–1869, Hettiarachchi et al., Aug. 1985.
J. Electrochem. Soc., vol. 127, No. 8, pp. 1745–1751, MacDonald et al., Aug. 1980.
J. Electrochem. Soc., vol. 126, No. 6, pp. 908–911, MacDonald et al., Jun. 1979.

Primary Examiner—John Niebling
Assistant Examiner—Bruce F. Bell

[57] ABSTRACT

A method and apparatus for the monitoring and control of concentration of an ion in a solution at an elevated temperature of at least 100° C. are disclosed. The method comprises the steps of contacting a first electrode with a flowing first solution containing said ion at the elevated temperature, and contacting a second electrode with a second flowing solution containing said ion at the elevated temperature. The rate of flow of the second solution is substantially lower than the rate of flow of the first solution. The first and second solutions are then contacted or admixed. The electrodes must be capable of detecting the ion at the elevated temperature and have the same response characteristics to changes in concentration of the ion at the elevated temperature. The concentration of the ion in the second solution is measured at a temperature lower than the elevated temperature under conditions permitting accurate measurement of the concentration of the ion, and the concentration of the ion in the first solution is monitored and controlled by adjusting the concentration of the ion in at least one of the first and second solutions. The method is particularly adapted for the monitoring and control of salt solutions used in the manufacture of polyamides, using palladium hydride electrodes.

3 Claims, 1 Drawing Sheet

MONITORING AND CONTROL OF PROCESS STREAMS AT ELEVATED TEMPERATURES

This is a division of application Ser. No. 07/829,845, filed Jan. 31, 1992, now U.S. Pat. No. 5,213,668.

BACKGROUND OF THE INVENTION

1. Field of the Invention

The present invention relates to a method and apparatus for the monitoring and control of the concentration of ions, especially hydrogen ions, in process streams at elevated temperatures. In a particular embodiment, the method and apparatus relate to monitoring and control of pH in processes for the manufacture of polyamides.

Polyamides are produced by thermal condensation of diacids with diamines. The ratio of the diacid and diamine monomers must be very nearly stoichiometric in order to obtain a polymer having a high molecular weight. In practice, a concentrated solution of the salt of the diacid and diamine in water is prepared. The pH of this solution is very sensitive to the ratio of the two monomers and pH measurements are used to adjust the ratio with a high degree of accuracy. This may readily be accomplished in the case of the lower polyamides, e.g. polyhexamethylene adipamide which is also known as nylon 6/6, because 1,6-diaminohexane adipate salt is very soluble in water at ambient temperature. Concentrations of the salt of 50%, by weight, may easily be achieved, and are used as the feed stock for the polymerization process. The salt solution is usually prepared by admixing the monomers using a small excess of the diacid and then adding a solution of the diamine until the desired pH is obtained. Similar techniques may be used in continuous processes for preparing the salt solution for a polyamide polymerization process.

The salts required for the manufacture of the higher polyamides are less soluble in water at ambient temperature than 1,6-diaminohexane adipate salt. For example, the solubility of the salt of 1,12-diaminododecane and 1,12-dodecanedioic acid i.e. the salt for the manufacture of nylon 12/12, in water is much less than 1%, by weight, at ambient temperature. A solubility of the salt in water that is sufficient for feeding to a polymerization process is obtained only at temperatures of 120°-150° C. under increased pressures. However, pH cannot be monitored at these temperatures in a reliable manner; in practice, it becomes necessary to adjust the pH by small additions of one of the monomers, obtain a sample of the resultant solution and measure the pH on cooled, diluted solution. This procedure is time consuming and is not amenable to a continuous process for the manufacture of the salt.

If it is desired to use salt solutions which have relatively low water contents, to reduce the amount of water that must be removed during the subsequent polymerization process, or use molten salt obtained from molten anhydrous ingredients, then any measurements on and monitoring of the salt solution must be conducted at elevated temperatures.

The problems described above that are encountered in the production of higher polyamides or in the use of anhydrous salts are primarily those of measurement of pH at elevated temperatures. It is an illustration of the broader problem of conducting measurements of concentrations of ions at elevated temperature.

The electrodes used in the measurement of ion concentrations are often based on a conductive glass membrane. Such electrodes are used in conjunction with a reference electrode connected with the medium of the ion being measured via a salt bridge. This system is reliable at ambient or slightly elevated temperatures. However, at higher temperatures, the glass membrane tends to degrade, with the rate of this degradation depending on the nature of the medium. Thus, for example, degradation tends to be more rapid in an alkaline solution. Glass electrodes cannot be used at temperatures higher than about 130° C. in mild environments and about 100° C. in alkaline or other corrosive solutions.

Some electrically conductive ceramic materials can be substituted for the glass membrane in ion selective electrodes, but ceramic materials only conduct electricity at temperatures above about 180° C. For example, pH sensors using stabilized zirconia ceramic membranes have been described by S. Hettiarachchi et al., J. Electrochem. Soc., 1985, 132 (8), 1866.

Electrodes that do not have membranes may also be used for measuring ion concentrations in solutions at elevated temperatures. Palladium hydride was used for pH measurements by D. D. Macdonald et al., J. Electrochem. Soc. 1980, 127 (8), 1745. Similarly, use of palladium hydride electrodes was described by J. V. Dobson in U.S. Pat. No. 4 242 189, issued 1980 Dec. 30; the state of the electrode was monitored by measuring its resistance since the resistance of palladium metal is much lower than that of palladium hydride.

The design of a high temperature reference electrode and of the salt bridge are equally important. The reference electrode may be either internal, i.e. located close to the measurement electrode at the system temperature, or external i.e. operated at ambient temperature and connected with the system by a salt bridge. Although a design described by D. D. Macdonald (J. Electrochem, Soc., 1979 (6), 908) may be suitable for measurements of short duration in relatively clean environments, performance would be expected to degrade with time, particularly in streams containing large concentrations of polymerizable or unstable components, and not be reliable for monitoring a process over an extended period of time.

A further complication of high temperature measurements of ion concentration is that of interpretation of the data obtained. The ion concentration is inferred from the measured potential of the measuring electrode. However, in equilibrium systems, such as in the measurement of pH, the measured potential will not provide useful information on the status of the system, unless the temperature dependence of the equilibrium constants involved is known. Thus, for example, the potential of a pH electrode in a "neutral" concentrated solution of a polyamide salt solution is quite dependent on the solution temperature, making it difficult to interpret and theoretically predict the amount of adjustment needed to obtain a predetermined composition.

SUMMARY OF THE INVENTION

A method for the monitoring and control of concentrations of ions at elevated temperatures has now been found.

Accordingly, the present invention provides a method for the monitoring or control of concentration of an ion in a solution at an elevated temperature, said temperature being at least 100° C., comprising the steps of:

(a) contacting a first electrode with a flowing first solution containing said ion at the elevated temperature, said electrode being capable of detecting said ion at the elevated temperature;

(b) contacting a second electrode with a flowing second solution containing said ion at the elevated temperature, said second electrode being capable of detecting said ion, the rate of flow of the second solution being substantially lower than the rate of flow of the first solution and the concentration of the ion in the second solution having been measured at a temperature lower than the elevated temperature under conditions permitting accurate measurement of the concentration of the ion, and the second electrode having the same response characteristics to changes in concentration of said ion at the elevated temperature as the first electrode; and (c) contacting the second solution with the first solution, the concentration of the ion in the first solution being monitored and controlled by adjusting the concentration of the ion in at least one of the first and second solutions.

In a preferred embodiment of the method of the present invention, the first and second electrodes are identical.

In another embodiment, the ion is hydrogen ion and, preferably, the electrode is a palladium hydride electrode.

In yet another embodiment, the ratio of the rate of flow of the first solution to that of the second solution is at least 50:1 and preferably at least 100:1.

The present invention also provides apparatus for the monitoring or control of concentration of an ion in a solution at a temperature of at least 100° C., comprising:

(a) a first electrode adapted to be in contact with a first solution at said temperature, said first solution being that having the ion that is to be monitored and controlled, said electrode being capable of detecting said ion at the elevated temperature;

(b) a second electrode adapted to be in contact with a second solution at said temperature in a chamber, said second solution containing the ion and the second electrode being capable of detecting the ion at the elevated temperature, the second electrode having the same response characteristics to changes in concentration of said ion at the elevated temperature as the first electrode; and (c) a fluid flow passage for the second solution from an inlet to said chamber, and subsequently for discharge of the second solution from the chamber, the fluid passage for discharge of the second solution being in fluid flow communication with the first solution.

In a preferred embodiment of the apparatus, the electrodes are adapted for the detection of hydrogen ions.

In another embodiment, the electrodes are identical.

In a further embodiment, the fluid passage for discharge of the second solution into the first solution is a restricted passage, especially a capillary.

BRIEF DESCRIPTION OF THE DRAWING

The present invention will be particularly described with reference to the embodiment shown in the drawing in which:

FIG. 1 shows an ion measuring device generally indicated by 1. Measuring device 1 has a first electrode 2, a second electrode 3 and an inlet 4 for second solution 20 (not shown). In preferred embodiments, both electrodes are palladium hydride electrodes which may be regenerated in situ by periodically polarizing the electrodes, as is described below. First electrode 2 extends through electrode port 5, steel block 6 and insulating block 7; insulating block 7 is conveniently formed from an inert material e.g. Teflon ® fluoropolymer. Tip 8 of first electrode 2 that extends beyond lower face of insulating block 7 would normally be in contact with first solution, which is generally indicated by 9.

Figure 1:
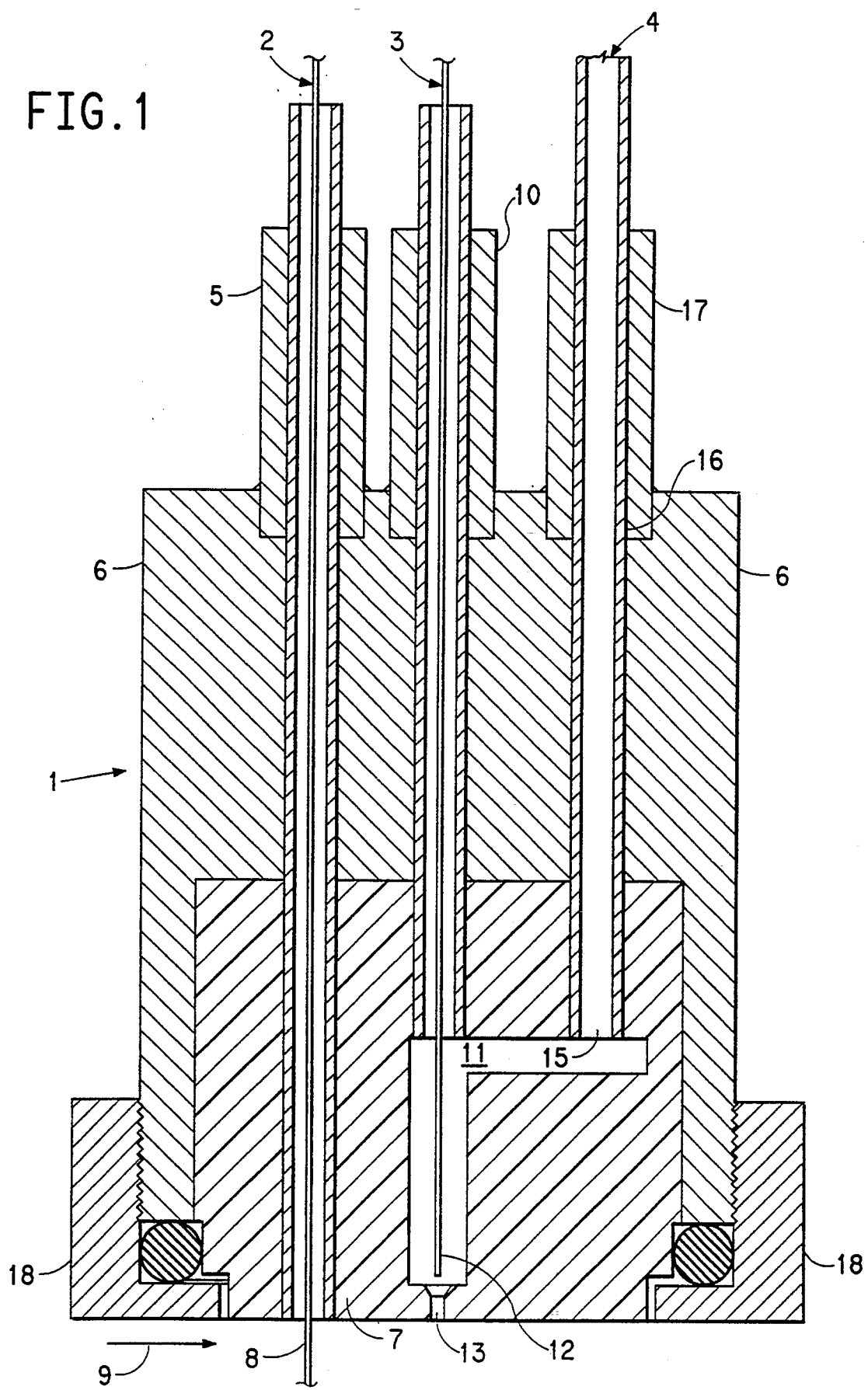
FIG. 1 is a schematic representation of apparatus used in the present invention.

Second electrode 3 extends through electrode port 10, through steel block 6 and into chamber 11; chamber 11 is located in insulating block 7. Tip 12 of second electrode 3 extends into chamber 11 to a location juxtaposed to outlet 13 from chamber 11; outlet 13 is preferably a restricted outlet e.g- a capillary. At a location in chamber 11 opposed to outlet 13 is inlet 15. Inlet 15 and inlet 4 are connected together by pipe 16 that extends through port 17 and blocks 6 and 7.

Steel block 6 is located in the walls of a vessel, indicated by 18, used in the processing of a solution at elevated temperatures.

In operation, a first solution is passed, at elevated temperature, by tip 8 of the first electrode 2. A second solution 20 is fed into inlet 4, passed through tube 16 into chamber 11, passed by tip 12 of second electrode 4 and exits from chamber 11 through outlet 13, and is admixed with the first solution. The second solution is at the same elevated temperature as the first solution, or is heated to such temperature by steel block 6 prior to entry into chamber 11. The rate of flow of the second solution is substantially lower than that of the first solution; in preferred embodiments, the rate of flow of the second solution is 50 times lower than that and especially 100 times lower than that of the first solution. In addition, since the solutions are to be contacted, or admixed, as shown in FIG. 1, the second solution needs to be inert to or compatible with the first solution. While reference is made herein to contact or admixing of the first and second solutions, the more fundamental requirement is to satisfy the electrochemical requirements imposed by the method of measurement.

In a separate step performed on second solution 20 prior to its introduction to inlet 4, the concentration of the ion being monitored is measured at a lower temperature e.g. at ambient temperature, using techniques that are known to give accurate results.

DESCRIPTION OF THE PREFERRED EMBODIMENTS

Several modes of operation may be used. For instance, in the measurement of pH, the pH of the second solution may be measured at ambient temperature and adjusted until the first and second electrodes, 2 and 3, show the same readings i.e. a null reading between them. At that point, the pH of the first solution will be known to be that of the second solution. Alternatively, the pH of the first solution could be adjusted until the electrodes gave the same readings, thereby adjusting the pH of first solution 9 to a predetermined value i.e. that of second solution 20. In a continuous operation using a second solution of predetermined composition, the pH of the first solution may be monitored and adjusted to maintain the pH of the first solution at the predetermined value. This could be a critical method in the monitoring and control of a process.

The present invention has been described with particular reference to the use of palladium hydride electrodes. However, other ion-specific electrodes may be used in the monitoring and control of solutions at elevated temperatures, especially in the monitoring and control of ion concentrations in solutions at elevated temperatures e.g. conductive alumina electrodes. Furthermore, while the concepts of the apparatus described with reference to FIG. 1 would remain the same, other physical arrangements may be used, especially if the electrodes are other than palladium hydride. The preferred solutions are aqueous solutions, but other solutions capable of being subjected to electrochemical measurements may be used.

It is important that the electrodes have the same response characteristics to the ion being monitored or controlled, at the elevated temperatures. In preferred embodiments, the electrodes are identical, but the electrodes may be different provided that the response of both electrodes to changes in ion concentration is the same at the temperature of use. For example, if the electrodes are to be used for comparing identical solutions, a null reading should be obtained over the range of temperatures that are to be used, regardless of ion concentration. Thus, identical electrodes are preferred.

The present invention is particularly useful in the monitoring and control of salt solutions used in the polymerization of polyamides, and especially in the monitoring and control of such salt solutions in which the salt solutions must be or are maintained at elevated temperatures.

The present invention is illustrated by the following examples.

EXAMPLE I

The apparatus used was that shown in FIG. 1. Prior to assembly, the ends of first (measuring) electrode 2 and second (reference) electrode 3 were electroplated with palladium, using the following procedure. The electroplating bath contained 2% $PdCl_2$ in 1N hydrochloric acid. The electrodes were sequentially placed in the bath and connected to the cathode of a 9 V battery through a 330 ohm resistor. The anode of the battery was connected to a 0.5 mm platinum wire, which was also placed in the bath. The electrode was electroplated for 5 minutes. A black palladium coating was obtained.

Both electrodes were covered with Teflon ® fluoropolymer tubing and inserted into the apparatus through gas chromatograph-type swaged fittings 5 and 10. The apparatus comprised a stainless steel body 6 with insulating body 7 formed from Teflon ® fluoropolymer. The assembled apparatus was inserted into cavity 18 of a reactor containing process solution 9. A tight seal was provided by "O" ring 19.

The apparatus was assembled and attached to the bottom of a 25.4 mm (internal diameter) stirred reactor provided with a heating mantle and a pressure relief valve which would purge out any excess liquid e.g. from the reference solution, injected into the reactor. The reactor was filled with a solution (process solution 9). The reference solution 20 was pumped into the reactor by a syringe pump through inlet 4 into tube 16, which was 1.6 mm (OD) stainless steel tubing.

The palladium coated end 8 of measuring electrode 2 was in contact with process solution 9. The reference solution 20 was injected into stainless steel tube 15, from which it contacted palladium coated end 12 of reference electrode 3 in chamber 11, before passing through pinhole opening 13 into process solution 9 at a location removed from measuring electrode 2. Nitrogen was bubbled through both solutions to remove dissolved oxygen prior to measurements being taken.

In order to activate the electrodes, the electrodes were sequentially connected as follows: (a) both electrodes were connected together to the negative terminal of a 9 volt battery through a 250 ohm resistor, to charge the electrodes with hydrogen, and (b) both electrodes were connected together to the positive terminal of the 9 volt battery through a 250 ohm resistor, to discharge excess hydrogen from the electrodes. In both instances, the other battery terminal was connected to the body of the stirred vessel. As illustrated below, the period of time used to charge the electrodes was substantially longer than the period of discharge.

To conduct measurements, the electrodes were connected by coaxial cables to the respective terminals of a two pen chart recorder, with the ground of the recorder and of the coaxial shields being connected with the body of the stirred vessel. The input impedance of the recorder was greater than $10 \times 10^{10}$ ohms. The recorder thus registered the potential of the electrodes opposite the ground and each other.

The reactor was filled with a phosphate buffer solution having a pH of 7 at ambient temperature, this being process solution 9. The same solution was used as reference solution 20. The reactor pressure was set at 550 kPa and the reactor was heated to 140° C. The reference solution was injected at a rate of 0.5 mL/hr. The electrodes were charged for 20 minutes and then discharged for 8 seconds.

A steady reading of zero mV between the two electrodes was obtained.

The null reading obtained demonstrates that the apparatus may be used to compare the pH of two solutions at elevated temperature.

EXAMPLE II

The procedure of Example I was repeated, except that the reference solution was a buffer of pH=5.

A steady difference in the potential between the electrodes was observed. This result demonstrates that the apparatus will detect a difference in pH between two solutions at elevated temperature, and could be used in determination of pH of a solution or adjustment of a solution pH to a known or predetermined value.

EXAMPLE III

The vessel was filled with a solution of 1,6-diaminohexane adipate (nylon 6,6 salt), which had a pH of about 8 at room temperature. The same solution was used as the reference solution. The pressure in the vessel was set at 690 kPa and the temperature was 140° C. The reference solution was pumped at a rate of 0.5 mL/hr into inlet 4. The electrodes were charged for 10 minutes and discharged for 5 seconds.

A very steady reading of zero mV between the electrodes was obtained. This result demonstrates that the apparatus may be used at elevated temperature with solutions other than simple buffered aqueous solutions.

EXAMPLE IV

The procedure of Example III was repeated except that the vessel temperature was 150° C.

A steady ready of zero mV was obtained. This result demonstrates use of the apparatus at the higher temperature of 150° C.

I claim:

1. An apparatus for the monitoring and control of concentration of an ion at a temperature of at least 100° C., comprising:
    (a) a first electrode and a second electrode, said first and second electrodes being identical and capable of detecting an ion at said temperature;
    (b) said first electrode being positioned in a first fluid flow passage such that a solution flowing through said first fluid flow passage will be in continuous contact with said first electrode;
    (c) said second electrode being positioned in a second fluid flow passage such that a solution flowing through said second fluid flow passage will be in continuous contact with said second electrode; and
    (d) means for connecting said first and second fluid flow passage such that
        (1) a solution flowing through said first fluid flow passage is contacted with a fluid flowing through said second fluid flow passages, and
        (2) said second fluid flow passage is constructed such that the fluid flow rate therein is at least 50 times lower than the fluid flow rate in said first fluid flow passage.

2. The apparatus of claim 1 in which the electrodes are capable of detecting hydrogen ions.

3. The apparatus of claim 1 in which the means for connecting said first and second fluid flow passages is a capillary.

* * * * *